(12) United States Patent
Osaka et al.

(10) Patent No.: US 8,147,987 B2
(45) Date of Patent: Apr. 3, 2012

(54) ORGANIC ELECTROLUMINESCENT ELEMENT AND COMPOUNDS FOR USE IN THE ELEMENT

(75) Inventors: Itaru Osaka, Pittsburgh, PA (US);
Tatsuya Igarashi, Ashigarakami (JP);
Toshihiko Ise, Ashigarakami-gun (JP);
Eiji Fukuzaki, Ashigarkami-gun (JP);
Satoshi Sano, Ashigarakami-gun (JP)

(73) Assignee: Fujifilm Corporation, Tokyo (JP)

( * ) Notice: Subject to any disclaimer, the term of this patent is extended or adjusted under 35 U.S.C. 154(b) by 1058 days.

(21) Appl. No.: 11/709,829

(22) Filed: Feb. 23, 2007

(65) Prior Publication Data
US 2007/0202357 A1 Aug. 30, 2007

(30) Foreign Application Priority Data

Feb. 23, 2006 (JP) .................. 2006-047150

(51) Int. Cl.
*B32B 19/00* (2006.01)
*B32B 9/00* (2006.01)
*C07D 403/00* (2006.01)
*C07D 235/00* (2006.01)
*C07D 403/02* (2006.01)

(52) U.S. Cl. .................. 428/690; 257/E51.05; 428/917; 313/504; 313/506; 548/302.7; 548/304.4; 548/305.4

(58) Field of Classification Search .................. 428/690, 428/917; 313/504, 506; 548/103, 108, 402, 548/302.7, 304.4, 305.4; 546/4; 549/3, 209.212; 257/E51.05
See application file for complete search history.

(56) References Cited

U.S. PATENT DOCUMENTS

| | | | |
|---|---|---|---|
| 5,766,779 A * | 6/1998 | Shi et al. ..................... | 428/690 |
| 2005/0260441 A1 * | 11/2005 | Thompson et al. .......... | 428/690 |
| 2005/0260449 A1 * | 11/2005 | Walters et al. .............. | 428/690 |

FOREIGN PATENT DOCUMENTS

| | | |
|---|---|---|
| JP | 2002-100476 A | 4/2002 |
| JP | 2005-89544 A | 4/2005 |
| WO | WO 00-70655 A2 | 11/2000 |
| WO | WO2005/113704 A2 * | 12/2005 |

OTHER PUBLICATIONS

Wen Li Jia, Theresa McCormick, Ye Tao, Jian-Ping Lu, and Suning Wang, New Phosphorescent Polynuclear Cu(I) Compounds Based on Linear and Star-Shaped 2-(2'-Pyridyl)benzimidazolyl Derivatives: Syntheses, Structures, Luminescence, and Electroluminescence, Inorganic Chemistry, vol. 44, No. 16, 2005, 5706-5712. © 2005 American Chemical Society.*

Qin-De Liu, Wen-Li Jia, and Suning Wang, Blue Luminescent 2-(2'-Pyridyl)benzimidazole Derivative Ligands and Their Orange Luminescent Mononuclear and Polynuclear Organoplatinum(II) Complexes, Inorganic Chemistry, vol. 44, No. 5, 2005,1332-1343,© 2005 American Chemical Society.*

* cited by examiner

*Primary Examiner* — Mark Kopec
*Assistant Examiner* — Bijan Ahvazi
(74) *Attorney, Agent, or Firm* — Sughrue Mion, PLLC

(57) ABSTRACT

An organic electroluminescent element comprises: a pair of electrodes; and one or more organic compound layers at least one of which is a light-emitting layer, the one or more organic compound layers being provided between the pair of electrodes, wherein at least one of the one or more organic compound layers comprises a compound represented by general formula (Z):

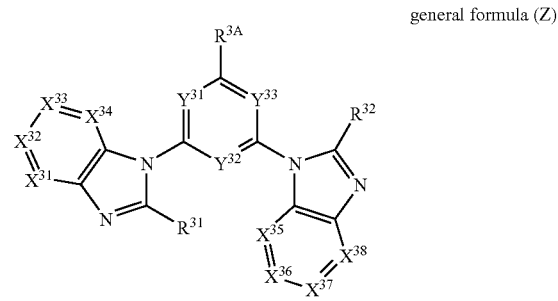

general formula (Z)

wherein $R^{31}$ and $R^{32}$ each represents a hydrogen atom or a substituent, $R^{3A}$ represents a substituent other than an aromatic hetero ring connected through a nitrogen atom, or a hydrogen atom, $X^{31}$ to $X^{38}$ each represents a substituted or unsubstituted carbon atom or a nitrogen atom, and $Y^{31}$ to $Y^{33}$ each represents a nitrogen atom or C—$R^{3B}$ (wherein $R^{3B}$ represents a substituent other than an aromatic hetero ring connected through a nitrogen atom, or a hydrogen atom).

11 Claims, No Drawings

ORGANIC ELECTROLUMINESCENT ELEMENT AND COMPOUNDS FOR USE IN THE ELEMENT

BACKGROUND OF THE INVENTION

1. Field of the Invention

The present invention relates to a light-emitting element which can convert electric energy to light to emit light, in particular, to an organic electroluminescent element and novel compounds to be used therein.

2. Description of the Related Art

An organic electroluminescent (EL) element has attracted attention since it can provide luminescence with a high luminance at a low voltage. As an important characteristic value of this organic electroluminescent element, there exists external quantum efficiency. The external quantum efficiency is calculated by the formula of "external quantum efficiency $\phi$=a number of photons emitted from an element/a number of electrons injected into the element".

An element having higher external quantum efficiency can be said to be advantageous in view of electric power consumption.

The external quantum efficiency of an organic electroluminescent element is determined according to the formula of "external quantum efficiency $\phi$=internal quantum efficiency× light extraction efficiency". In an organic EL element utilizing fluorescent luminescence from an organic compound, the limit value of internal quantum efficiency is 25%, and light extraction efficiency is about 20%, and hence the limit value of external quantum efficiency is believed to be about 5%.

As a method of improving external quantum efficiency of an element by improving the internal quantum efficiency of an organic electroluminescent element, an element (a triplet light-emitting element) using a triplet light-emitting material (phosphorescent luminescence material) has been reported (WO00/070655). In comparison with conventional elements utilizing fluorescent luminescence (singlet light-emitting element), this element can improve the external quantum efficiency, and the maximum value of the external quantum efficiency of an element using Ir(ppy)$_2$ which is a green-color phosphorescent material has amounted to 8% (external quantum efficiency upon 100 cd/m$^2$: 7.5%). On the other hand, in order to apply an element using a triplet light-emitting material to a full-color display or a white light-emitting element, there has been demanded an element capable of generating luminescence with a high efficiency in the other colors, particularly in the blue region.

An element has recently been reported which uses a light-emitting material capable of emitting a light of 500 nm or less in maximal luminescence and a host material having the lowest triplet energy level lower than that of the light-emitting material (JP-A-2002-100476). In comparison with conventional host materials, this element can improve the external quantum efficiency, but has been demanded to improve in view of durability.

Further, there has been proposed an organic electroluminescent element employing a compound in which a plurality of imidazole skeletons is connected through a linking group (JP-A-2005-89544), but there are problems in that a lowest triplet energy level is low and when it is employed as a material for a triplet light-emitting element (particularly as a material constituting a light-emitting layer or a layer adjacent to the light-emitting layer), a luminous efficiency for the element lowers.

SUMMARY OF THE INVENTION

An object of the invention is to provide a light-emitting element having high efficiency and good durability and novel compounds for use in the element.

The constitution for solving the above-mentioned problems is as follows.

[1] An organic electroluminescent element comprising: a pair of electrodes; and one or more organic compound layers at least one of which is a light-emitting layer, the one or more organic compound layers being provided between the pair of electrodes, wherein at least one of the one or more organic compound layers comprises a compound represented by general formula (Z):

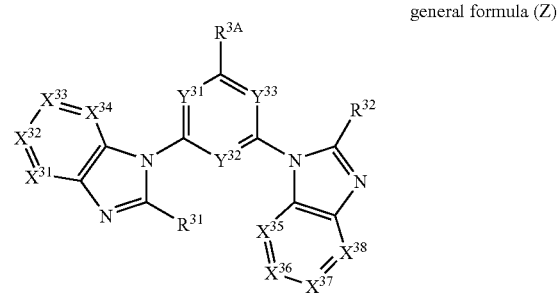

general formula (Z)

wherein R$^{31}$ and R$^{32}$ each represents a hydrogen atom or a substituent, R$^{3A}$ represents a substituent other than an aromatic hetero ring connected through a nitrogen atom, or a hydrogen atom, X$^{31}$ to X$^{38}$ each represents a substituted or unsubstituted carbon atom or a nitrogen atom, and Y$^{31}$ to Y$^{33}$ each represents a nitrogen atom or C—R$^{3B}$ (wherein R$^{3B}$ represents a substituent other than an aromatic hetero ring connected through a nitrogen atom).

[2] The organic electroluminescent element as described in [1] above, wherein the compound represented by the general formula (Z) is a compound represented by the following general formula (Z-2):

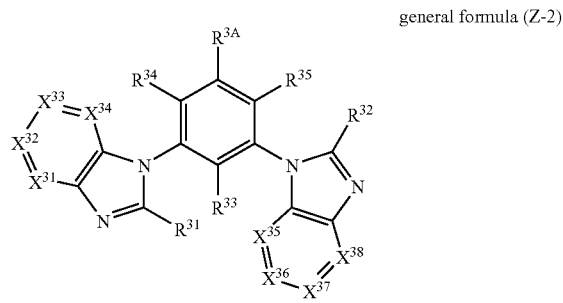

general formula (Z-2)

wherein R$^{31}$ and R$^{32}$ each represents a hydrogen atom or a substituent, R$^{33}$ to R$^{35}$ and R$^{3A}$ each represents a substituent other than an aromatic hetero ring connected through a nitrogen atom, or a hydrogen atom, and X$^{31}$ to X$^{38}$ each represents a substituted or unsubstituted carbon atom or a nitrogen atom.

[3] The organic electroluminescent element as described in [2] above, wherein the compound represented by the general formula (Z-2) is a compound represented by the following general formula (Z-3):

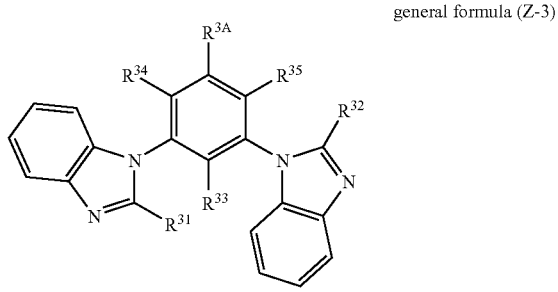

general formula (Z-3)

wherein $R^{31}$ and $R^{32}$ each represents a hydrogen atom or a substituent, and $R^{33}$ to $R^{35}$ and $R^{34}$ each represents a substituent other than an aromatic hetero ring connected through a nitrogen atom, or a hydrogen atom.

[4] The organic electroluminescent element as described in any one of [1] to [3] above, wherein the light-emitting layer comprises a compound capable of generating luminescence by a transition from a triplet excitation state thereof.

[5] The organic electroluminescent element as described in any one of [1] to [4] above, wherein the compound represented by the general formula (Z) is contained in the light-emitting layer.

[6] The organic electroluminescent element as described in any one of [1] to [5] above, wherein the compound represented by the general formula (Z) is contained in one of the organic compound layers which is adjacent to the light-emitting layer.

[7] The organic electroluminescent element as described in any one of [1] to [6] above, wherein the lowest triplet energy level of the compound represented by the general formula (Z) is 65 kcal/mol or more.

[8] A compound represented by the above-described general formula (Z).

[9] A compound represented by the above general formula (Z-2).

[10] A compound represented by the above general formula (Z-3).

DETAILED DESCRIPTION OF THE INVENTION

The organic electroluminescent element of the invention is an organic electroluminescent element (hereinafter also referred to as "element of the invention", "light-emitting element" or "EL element") having at least one organic compound layer (hereinafter also referred to as "organic layer") including a light-emitting layer between a pair of electrodes and is characterized in that a compound represented by the general formula (Z) in at least one of the organic compound layers. This constitution can provide a light-emitting element showing good light-emitting efficiency and good durability.

As is described above, the organic electroluminescent element of the invention has at least one light-emitting layer as an organic compound layer and, as organic compound layers other than the light-emitting layer, there may properly be disposed a hole injecting layer, a hole transporting layer, an electron blocking layer, an exciton blocking layer, a hole blocking layer, an electron transporting layer, an electron injecting layer and a protective layer, with each layer optionally having functions of other layer as well. Also, each layer may be constituted by plural layers.

The compound represented by the general formula (Z) is incorporated preferably in either or both of the light-emitting layer and the organic compound layer adjacent to the light-emitting layer, more preferably in the light-emitting layer.

The amount of a compound represented by formula (Z) in each layer is preferably from 1 to 100% by weight, more preferably from 10 to 90% by weight, still more preferably from 10 to 70% by weight, particularly preferably from 15 to 50% by weight regarding the light-emitting layer. Regarding other layers than the light-emitting layer, the amount is preferably from 1 to 100% by weight, more preferably from 10 to 100% by weight, still more preferably from 30 to 100% by weight, particularly preferably from 50 to 100% by weight.

Hereinafter, compounds represented by the general formula (Z) to be added to the organic compound layers of the organic electroluminescent element of the invention will be described in detail.

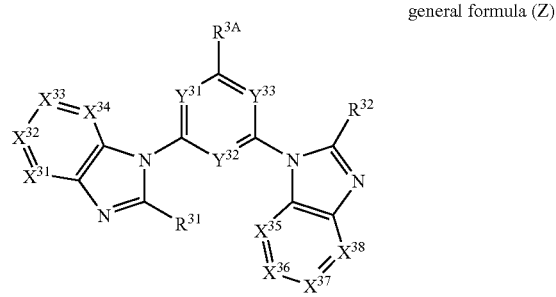

general formula (Z)

$R^{31}$ and $R^{32}$ each represents a hydrogen atom or a substituent. Examples of the substituent include the following substituent group A.

Substituent group A: an alkyl group (containing preferably from 1 to 30 carbon atoms, more preferably from 1 to 20 carbon atoms, particularly preferably from 1 to 10 carbon atoms; e.g., methyl, ethyl, iso-propyl, tert-butyl, n-octyl, n-decyl, n-hexadecyl, cyclopropyl, cyclopentyl or cyclohexyl), a perfluoroalkyl group (containing preferably from 1 to 30 carbon atoms, more preferably from 1 to 20 carbon atoms, particularly preferably from 1 to 10 carbon atoms; e.g., trifluoro methyl or pentafluoro methyl), an alkenyl group (containing preferably from 2 to 30 carbon atoms, more preferably from 2 to 20 carbon atoms, particularly preferably from 2 to 10 carbon atoms; e.g., vinyl, allyl, 2-butenyl or 3-pentenyl), an alkynyl group (containing preferably from 2 to 30 carbon atoms, more preferably from 2 to 20 carbon atoms, particularly preferably from 2 to 10 carbon atoms; e.g., propargyl or 3-pentynyl), an aryl group (containing preferably from 6 to 30 carbon atoms, more preferably from 6 to 20 carbon atoms, particularly preferably from 6 to 12 carbon atoms; e.g., phenyl, p-methylphenyl, naphthyl or anthranyl), an amino group (containing preferably from 0 to 30 carbon atoms, more preferably from 0 to 20 carbon atoms, particularly preferably from 0 to 10 carbon atoms; e.g., amino, methylamino, dimethylamino, diethylamino, dibenzylamino, diphenylamino, ditolylamino, dipyridylamino, dithienyl amino or phenylpyridylamino), an alkoxy group (containing preferably from 1 to 30 carbon atoms, more preferably from 1 to 20 carbon atoms, particularly preferably from 1 to 10 carbon atoms; e.g., methoxy, ethoxy, butoxy or 2-ethylhexyloxy), an aryloxy group (containing preferably from 6 to 30 carbon atoms, more preferably from 6 to 20 carbon atoms, particularly preferably from 6 to 12 carbon atoms; e.g., phenyloxy, 1-naphthyloxy or 2-naphthyloxy), a hetero ring oxy group (containing preferably from 1 to 30 carbon atoms, more preferably from 1 to 20 carbon atoms, particularly preferably from 1 to 12 carbon atoms; e.g., pyridyloxy, pyrazyloxy, pyrimidyloxy or quinolyloxy), an acyl group (containing preferably from 1 to 30 carbon atoms, more preferably from 1 to 20 carbon atoms, particularly preferably from 1 to 12 carbon atoms; e.g., acetyl, benzoyl, formyl or pivaloyl), an alkoxycarbonyl group (containing preferably from 2 to 30 carbon atoms, more preferably from 2 to 20 carbon atoms, particularly preferably from 2 to 12 carbon atoms; e.g., methoxycarbonyl or ethoxycarbonyl), an aryloxycarbonyl group (containing preferably from 7 to 30 carbon atoms, more preferably from 7 to 20 carbon atoms, particularly preferably from 7 to 12 carbon atoms; e.g., phenyloxycarbonyl), an acyloxy group (containing preferably from 2 to 30 carbon atoms, more preferably from 2 to 20 carbon atoms, particularly preferably from 2 to 10 carbon atoms; e.g., acetoxy or benzoyloxy), an acylamino group (containing preferably from 2 to 30 carbon atoms, more preferably from 2 to 20 carbon atoms, particularly preferably from 2 to 10 carbon atoms; e.g., acetylamino or benzoylamino), an alkoxycarbonylamimo group (containing preferably from 2 to 30 carbon atoms, more preferably from 2 to 20 carbon atoms, particularly preferably from 2 to 12 carbon atoms; e.g., methoxycarbonylamino), an aryloxycarbonylamino group (containing preferably from 7 to 30 carbon atoms, more preferably from 7 to 20 carbon atoms, particularly preferably from 7 to 12 carbon atoms; e.g., phenyloxycarbonylamino), a sulfonylamino group (containing preferably from 1 to 30 carbon atoms, more preferably from 1 to 20 carbon atoms, particularly preferably from 1 to 12 carbon atoms; e.g., methanesulfonylamino or benzenesulfonylamino), a sulfamoyl group (containing preferably from 0 to 30 carbon atoms, more preferably from 0 to 20 carbon atoms, particularly preferably from 0 to 12 carbon atoms; e.g., sulfamoyl, methylsulfamoyl, dimethylsulfamoyl or phenylsulfamoyl), a carbamoyl group (containing preferably from 1 to 30 carbon atoms, more preferably from 1 to 20 carbon atoms, particularly preferably from 1 to 12 carbon atoms; e.g., carbamoyl, methylcarbamoyl, diethylcarbamoyl or phenylcarbamoyl), an alkylthio group (containing preferably from 1 to 30 carbon atoms, more preferably from 1 to 20 carbon atoms, particularly preferably from 1 to 12 carbon atoms; e.g., methylthio or ethylthio), an arylthio group (containing preferably from 6 to 30 carbon atoms, more preferably from 6 to 20 carbon atoms, particularly preferably from 6 to 12 carbon atoms; e.g., phenylthio), a hetero ring thio group (containing preferably from 1 to 30 carbon atoms, more preferably from 1 to 20 carbon atoms, particularly preferably from 1 to 12 carbon atoms; e.g., pyridylthio, 2-benzimidazolylthio, 2-benzoxazolylthio or 2-benzothiazolylthio), a sulfonyl group (containing preferably from 1 to 30 carbon atoms, more preferably from 1 to 20 carbon atoms, particularly preferably from 1 to 12 carbon atoms; e.g., mesyl or tosyl), a sulfinyl group (containing preferably from 1 to 30 carbon atoms, more preferably from 1 to 20 carbon atoms, particularly preferably from 1 to 12 carbon atoms; e.g., methanesulfinyl or benzenesulfinyl), a ureido group (containing preferably from 1 to 30 carbon atoms, more preferably from 1 to 20 carbon atoms, particularly preferably from 1 to 12 carbon atoms; e.g., ureido, methylureido or phenylureido), a phosphoric acid amido group (containing preferably from 1 to 30 carbon atoms, more preferably from 1 to 20 carbon atoms, particularly preferably from 1 to 12 carbon atoms; e.g., diethylphosphoric acid amido or phenylphosphoric acid amido), a hydroxyl group, a mercapto group, a halogen atom (e.g., a fluorine atom, a chlorine atom, a bromine atom or an iodine atom), a cyano group, a sulfo group, a carboxyl group, a nitro group, a hydroxamic acid group, a sulfino group, a hydrazino group, an imino group, a hetero ring group (containing preferably from 1 to 30 carbon atoms, more preferably from 1 to 12 carbon atoms; hetero atom: e.g., nitrogen atom, oxygen atom, sulfur atom or silicon atom; specific examples being imidazolyl, pyridyl, quinolyl, furyl, thienyl, piperidyl, morpholino, benzoxazolyl, benzimidazolyl, benzothiazolyl, carbazolyl, azepinyl and silolyl), a silyl group (containing preferably from 3 to 40 carbon atoms, more preferably from 3 to 30 carbon atoms, particularly preferably from 3 to 24 carbon atoms; e.g., trimethylsilyl or triphenylsilyl) and a silyloxy group (containing preferably from 3 to 40 carbon atoms, more preferably from 3 to 30 carbon atoms, particularly preferably from 3 to 24 carbon atoms; e.g., trimethylsilyloxy or triphenylsilyloxy).

Among these substituents, an alkyl group, a perfluoroalkyl group, an aryl group, a hetero ring group, an alkenyl group, an alkoxy group, an aryloxy group, an alkylamino group, an arylamino group, a hetero ring amino group, a silicon-containing hetero ring group, a silyl group, a hydroxy group, a mercapto group, and a halogen atom are preferable, an alkyl group, a perfluoroalkyl group, an aryl group, a hetero ring group, an alkoxy group, an aryloxy group, an arylamino group, and a silyl group are more preferable, and an alkyl group, a perfluoroalkyl group, an aryl group, a hetero ring group, and a silyl group are still more preferable.

Herein, $R^{31}$ and $R^{32}$ may be the same as or different from each other.

$R^{3A}$ represents a substituent other than an aromatic hetero ring connected through a nitrogen atom, or a hydrogen atom. As the substituent, a substituent represented by the above substituent group A other than an aromatic hetero ring connected through a nitrogen atom may be applied, and examples preferably include an alkyl group, an aryl group, a hetero ring group, an alkenyl group, an alkoxy group, an aryloxy group, an alkylamino group, an arylamino group, a hetero ring amino group, a silicon-containing hetero ring group, a silyl group, a hydroxy group, a mercapto group, a halogen atom, and a cyano group, more preferably include an alkyl group, a perfluoroalkyl group, an aryl group, a hetero ring group, an alkoxy group, an aryloxy group, an arylamino group, a silyl group, and a cyano group, and still more preferably include an alkyl group, a perfluoroalkyl group, an aryl group, a hetero ring group, a silyl group, and a cyano group.

$X^{31}$ to $X^{38}$ each represents a substituted or unsubstituted carbon atom or a nitrogen atom. The substituent on the carbon atom is not particularly limited, but the substituent group A can be applied.

When $X^{31}$ to $X^{38}$ are each a carbon atom, the substituent on the carbon atom is preferably an alkyl group, an aryl group, a hetero ring group, an alkenyl group, an alkoxy group, an aryloxy group, an alkylamino group, an arylamino group, a hetero ring amino group, a silicon-containing hetero ring group, a silyl group, a hydroxyl group, a mercapto group or a halogen atom, more preferably an alkyl group, an aryl group, a hetero ring group, an alkoxy group, an aryloxy group, an arylamino group or a silyl group, still more preferably an alkyl group, an aryl group, a hetero ring group or a silyl group.

$Y^{31}$ to $Y^{33}$ each represents a nitrogen atom or C—$R^{3B}$. $R^{3B}$ is the same as $R^{3A}$ described hereinbefore, and the preferred scope thereof is also the same as described there.

The compound represented by the general formula (Z) is more preferably the compound represented by the general formula (Z-2). Next, the compound represented by the general formula (Z-2) will be explained.

In the general formula (Z-2), $R^{31}$, $R^{32}$, $R^{34}$, and $X^{31}$ to $X^{38}$ are the same as those in the general formula (Z), and the preferred scope thereof is also the same as described there. $R^{33}$ to $R^{35}$ and $R^{34}$ each represents a substituent other than an aromatic hetero ring connected through a nitrogen atom, or a hydrogen atom. The preferred scope of the group represented by $R^{33}$ to $R^{35}$ is also the same as for $R^{34}$ described hereinbefore.

The compound represented by the general formula (Z-2) is more preferably the compound represented by the general formula (Z-3). Next, the compound represented by the general formula (Z-3) will be explained.

In the general formula (Z-3), $R^{31}$, $R^{32}$, $R^{34}$, and $R^{33}$ to $R^{35}$ are the same as those in the general formula (Z-2), and the preferred scope thereof is also the same as described there.

The compounds represented by the general formulae (Z), (Z-2) and (Z-3) may be incorporated in any organic layer, but are preferably incorporated in the organic compound layer adjacent to the light-emitting layer or the light-emitting layer, more preferably in the light-emitting layer. Also, they may be incorporated in one organic layer or a plurality of organic layers.

The $T_1$ level (the energy level of the lowest triplet excitation state) of the compound represented by the general formula (Z) in a film state is preferably 45 kcal/mol (188.3 kJ/mol) or more, more preferably 55 kcal/mol (251.0 kJ/mol) or more, still more preferably 60 kcal/mol (272.0 kJ/mol) or more, particularly preferably 65 kcal/mol (294.7 kJ/mol) or more. Additionally, the upper limit is preferably 85 kcal/mol (355.6 kJ/mol) or less.

In particular, when the light-emitting layer contains a compound which generates luminescence from the triplet excitation state, the $T_1$ level of the compound represented by the general formula (Z) in the film state is preferably within the above-mentioned range.

The $T_1$ level can be determined by measuring phosphorescence spectrum of a compound in the film state and using the wavelength of the spectrum on the shorter wavelength side.

Next, examples of the compounds of the invention are shown below which, however, do not limit the invention in any way.

(1)

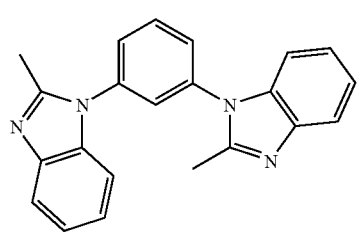

(2)

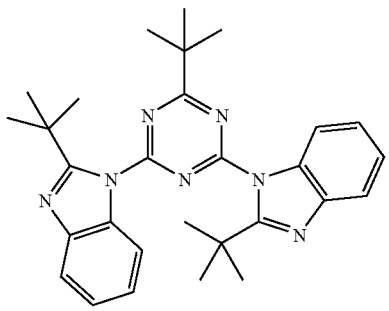

(3)

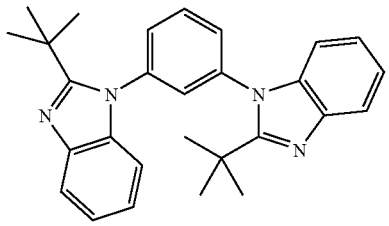

(4)

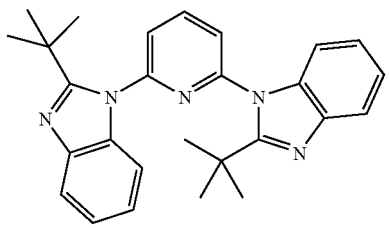

(5)

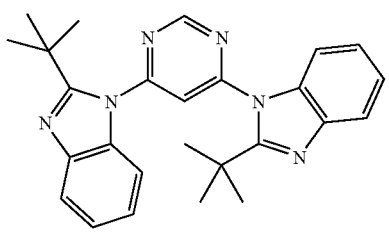

(6)

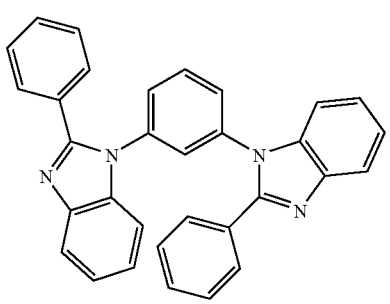

(7)

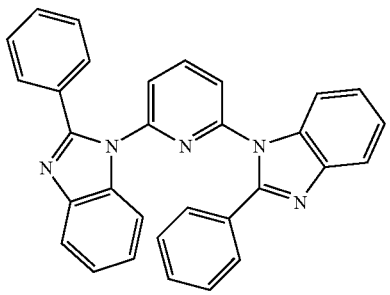

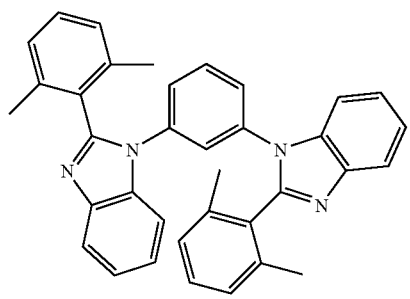
(8)
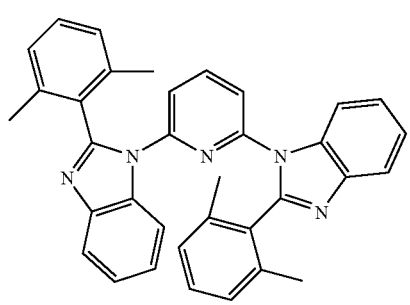
(9)
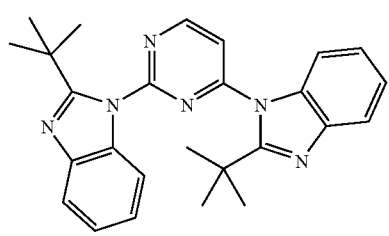
(11)
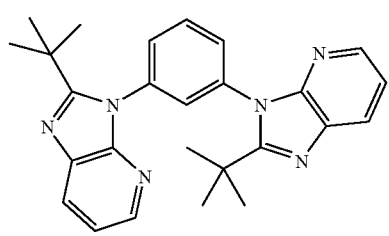
(12)
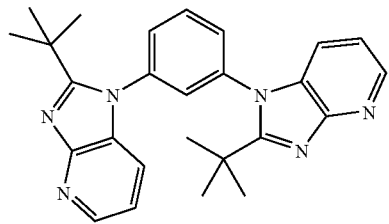
(13)
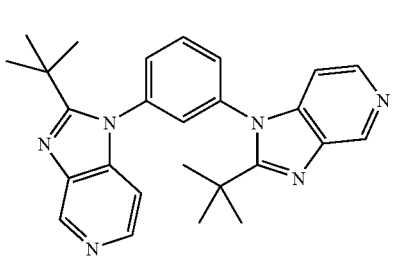
(14)
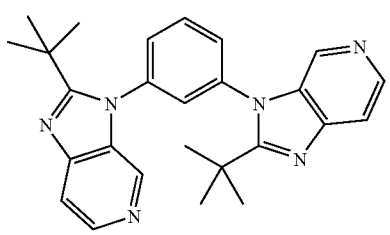
(15)
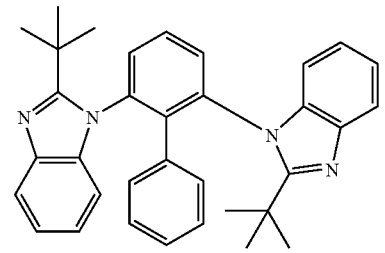
(19)
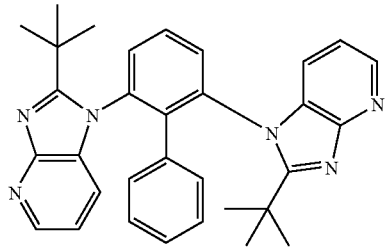
(20)
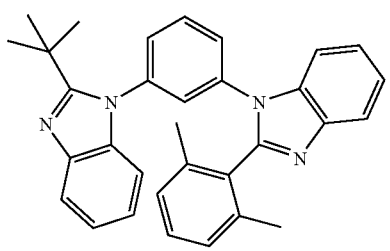
(23)
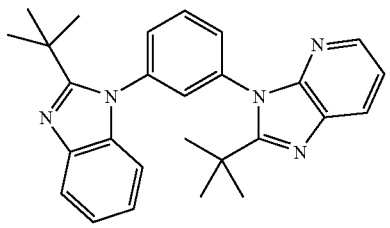
(24)
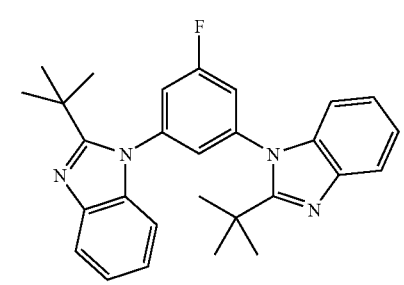
(29)

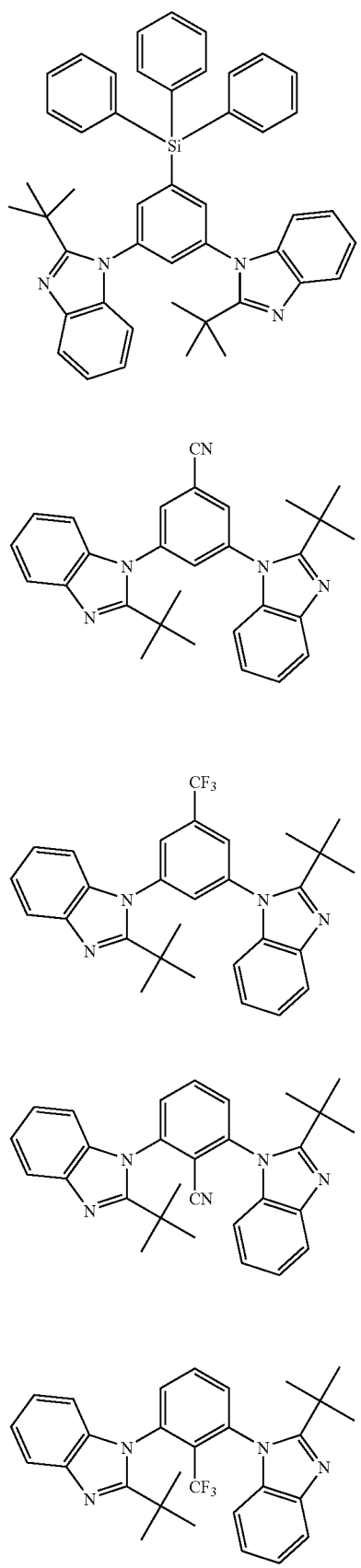
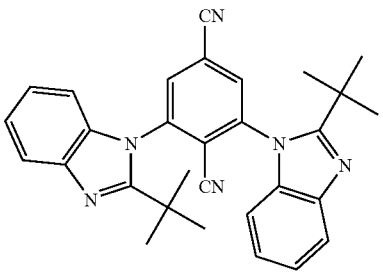
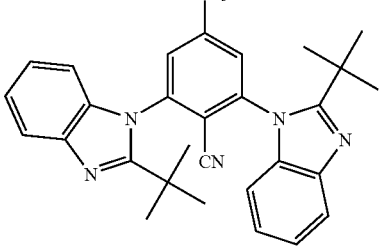
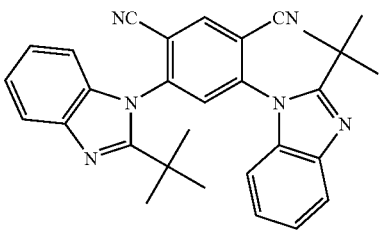
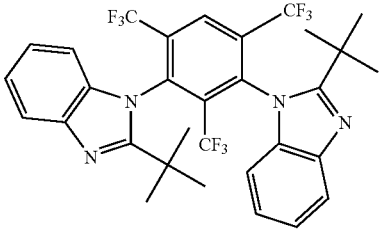
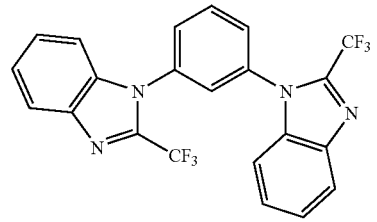
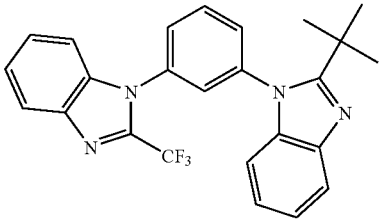
The compounds of the invention can be synthesized according to, for example, methods described in *Heterocycles*, Vol. 55, No. 5, 2001, 905-924.
Compounds represented by formula (Z) can be synthesized by employing various known methods. For example, they can be synthesized by reacting an aryl halide, an aryl triflate, a heteroaryl halide or a heteroaryl triflate with an imidazole derivative in the presence or absence of a catalyst (Pd or Cu), a base (carbonate, alkoxide or amine derivative), a solvent (a hydrocarbon series solvent, a halogen-containing solvent, an ether series solvent, an alcohol series solvent or water). They can also be synthesized by reacting an amine derivative with an aryl halide, an aryl triflate, a heteroaryl halide or a heteroaryl triflate, then conducting imidazole ring-forming reaction.

The process for synthesizing the compound of the invention will be described hereinafter.

SYNTHESIS EXAMPLE

Synthesis of Illustrative Compound 3

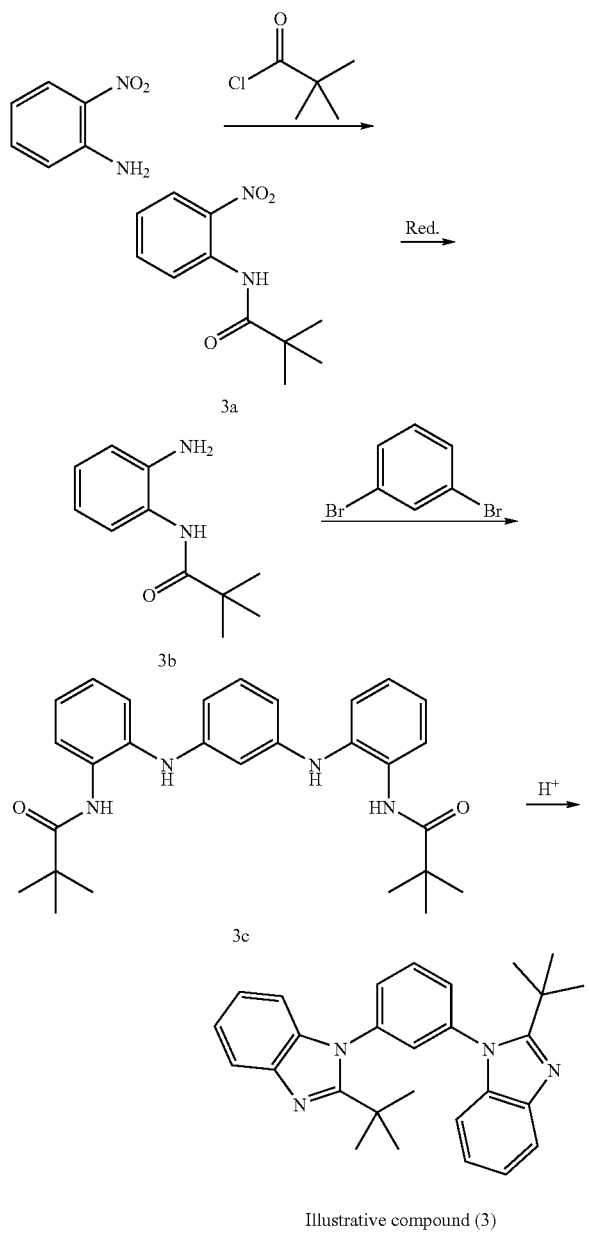

Illustrative compound (3)

[Synthesis of Compound 3a]

41.4 g (0.3 mol) of 2-nitroaniline, 39.8 g (0.33 mol) of pivalyl chloride and 250 mL of toluene were charged in a 1-L round bottom flask, and the mixture was stirred under an atmosphere of nitrogen. After refluxing for 1 hour under heating, the reaction solution was cooled to room temperature. 300 mL of ethyl acetate and 300 mL of distilled water were added thereto and, after extraction, the organic layer was further washed with 300 mL of distilled water, followed by drying the organic layer over magnesium sulfate. After filtering off magnesium sulfate, the reaction solution was concentrated under reduced pressure to obtain 66.8 g (0.3 mol) of compound 3a. Yield: 100%.

[Synthesis of Compound 3b]

66.8 g (0.3 mol) of compound 3a and 250 mL of ethanol were charged in a 1-L round bottom glask, followed by stirring under the atmosphere of nitrogen. 10 g of Pd—C of 55% in water content was added thereto, and the mixture was refluxed. Further, 47.3 g (0.75 mol) of ammonium formate was gradually added thereto. After refluxing for 1 hour under heating, the reaction solution was filtered through Celite. The filtrate was concentrated to a 2-fold thick concentration, followed by cooling in ice-water to obtain 34.6 g (0.18 mol) of compound 3b as flesh-colored crystals. Yield: 60%.

[Synthesis of Compound 3c]

6.34 g (33 mmols) of compound 3b, 3.54 g (15 mmols) of 1,3-dibromobenzene, 0.34 g (1.5 mmols) of palladium acetate, 1.34 g (4.5 mmols) of 2-(di-t-butylphosphino)biphenyl, 13.9 g (60 mmols) of rubidium carbonate and 100 mL of toluene were charged in 500 mL of toluene, followed by stirring in the atmosphere of nitrogen. After refluxing for 4 hours under heating, the reaction solution was filtered. After concentrating the filtrate, the concentrate was purified by silica gel column chromatography (developing solvent: hexane/ethyl acetate=5/2) to obtain 4.4 g (9.6 mmols) of compound 3c. Yield: 64%.

[Synthesis of Illustrative Compound 3]

4.4 g (9.6 mmols) of compound 3c and 50 mL of xylene were charged in a 300-mL round bottom flask, followed by stirring. 10 mL of acetic acid and 5 mL of 35% hydrochloric acid were added thereto, and the resulting mixture was refluxed for 2 hours under heating. After cooing to room temperature, 200 mL of chloroform and 300 mL of distilled water were added thereto, and the mixture was stirred at room temperature. Further, sodium hydrogen carbonate was added to render the mixed solution basic. The organic layer was dried over magnesium sulfate, and then concentrated. The thus-obtained solid product was refluxed under heating in 100 mL of methanol to obtain 1.2 g (2.8 mmols) of illustrative compound 3 as white powder. Yield: 30%.

The product was identified as the end compound by measurement of NMR and MS.

SYNTHESIS EXAMPLE 2

Synthesis of Illustrative Compound (31)

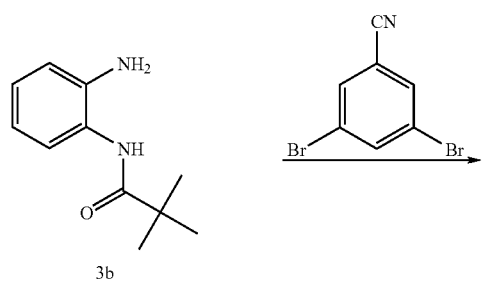

31a

Illustrative compound (31)

[Synthesis of Compound 31a]

8.1 g (42.16 mmol) of the compound 3b, 5 g (19.16 mmol) of 3,5-dibromobenzonitril, 17.7 g (76.65 mmol) of rubidium carbonate, 183 mg (0.38 mmol) of 2-dicyclohexylphosphino-2',4',6'-triisopropylbiphenyl, and 100 mL of xylene were charged in a 300-mL three-necked round bottom flask, and the mixture was stirred under a nitrogen stream. The solution was heated to a temperature of 50° C., and added with 43 mg (0.19 mmol) of palladium acetate. The solution was heated to a temperature of 115° C., and stirred with heating for 1 hour. The solution was cooled back to 100° C., and filtered while heating to remove insolubles. After distilling off the filtrate under reduced pressure and removing the solvent, recrystallization from ethyl acetate was carried out to obtain 6.22 g of a compound 31a as a white crystal (yield: 67%).

[Synthesis of Illustrative Compound (31)]

6.22 g (12.86 mmol) of the compound 31a, 1.22 g (6.43 mmol) of paratoluenesulfonic acid.monohydrate, and 50 mL of 4-t-butyl-o-xylene were charged in a 300-mL three-necked round bottom flask, and the mixture was stirred under a nitrogen stream. The solution was heated to a temperature of 190° C., and stirred with heating for 5 hours. The solution was cooled back to room temperature to give a gray precipitate. The obtained precipitate was isolated and purified with a silica gel column (hexane:ethyl acetate=1:1) to obtain 2.61 g of an illustrative compound (31) as a white crystal (yield: 45%).

The compound was identified as the end compound by measurement of NMR and MS.

SYNTHESIS EXAMPLE 3

Synthesis of Illustrative Compound (33)

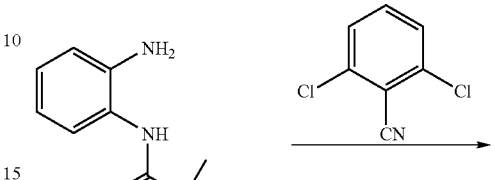

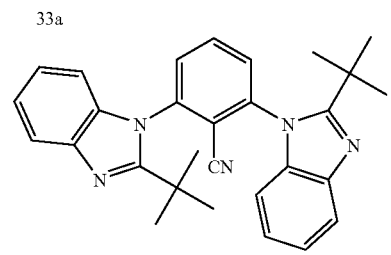

33a

Illustrative compound (33)

[Synthesis of Compound 33a]

20 g (0.104 mol) of the compound 3b, 8.52 g (49.5 mmol) of 2,6-dichlorobenzonitril, 47.4 g (0.198 mol) of rubidium carbonate, 2.21 g (7.43 mmol) of 2-(di-t-butylphosphino) biphenyl, 557 mg (2.48 mmol) of palladium acetate, and 318 mL of toluene were charged in a 1,000-mL three-necked round bottom flask, and the mixture was stirred under a nitrogen stream. The mixture solution was heated to a temperature of 80° C., and stirred with heating for 5 hours. The solution was cooled back to room temperature, and filtered to remove insolubles. The filtrate was extracted with ethyl acetate, subsequently washed with water and saturated saline in the order of precedence, and the organic phase was dried over magnesium sulfate. The solvent was distilled off under reduced pressure to obtain 21 g of a compound 33a as a white crystal (yield: 88%).

[Synthesis of Illustrative Compound (33)]

20 g (41.4 mmol) of the compound 33a, 15.8 g (82.8 mmol) of paratoluenesulfonic acid.monohydrate, and 100 mL of benzonitril were charged in a 300-mL three-necked round bottom flask, and the mixture was stirred under a nitrogen stream. The solution was heated to a temperature of 180° C., and stirred with heating for 16 hours. The reaction mixture was cooled back to room temperature. The resultant was extracted with ethyl acetate, washed with water and saturated saline in order of precedence, and the organic phase was dried over magnesium sulfate. The solvent was distilled off under reduced pressure, and recrystallization from an ethyl acetate-hexane solution was carried out to obtain 1.3 g of an illustrative compound (33) as a white crystal (yield: 7%).

The compound was identified as the end compound by measurement of NMR and MS.

Next, the organic electroluminescent element of the invention will be described below. The organic electroluminescent element of the invention does not require any particular system, driving method and utilizing embodiment. As a typical organic electroluminescent element, there can be illustrated an organic EL (electroluminescence) element.

The external quantum efficiency of the light-emitting element of the invention is preferably 5% or more, more preferably 10% or more, still more preferably 13% or more. As the numerical value of external quantum efficiency of the element, the maximal value of external quantum efficiency when the element is driven at 20° C. or a value of external quantum efficiency at around 100 to 300 cd/m$^2$ (preferably 200 to 300 cd/m$^2$) when the element is driven at 20° C. can be used.

The internal quantum efficiency of the light-emitting element of the invention is preferably 30% or more, more preferably 50% or more, still more preferably 70% or more. The internal quantum efficiency of an element is calculated according to the formula of: internal quantum efficiency=external quantum efficiency/light extraction efficiency. With ordinary organic EL elements, the light extraction efficiency is about 20%. However, the light extraction efficiency can be made 20% or more by devising shape of the substrate, shape of the electrodes, thickness of the organic layer, thickness of the inorganic layer, refractive index of the organic layer and refractive index of the inorganic layer.

The glass transition points of the host material incorporated in the light-emitting layer of the invention, materials incorporated in the electron transporting layer and hole transporting materials are preferably from 90° C. to 400° C., more preferably from 100° C. to 380° C., still more preferably from 120° C. to 370° C., particularly preferably from 140° C. to 360° C.

Here, Tg can be confirmed by thermal measurement such as differential scanning calorimetry (DSC) or differential thermal analysis (DTA), by X-ray diffractiometry (XRD) or by observation under a polarizing microscope.

Light-emitting materials to be used in the invention will be described below. Light-emitting materials are compounds which substantially exert the function of emitting light in a light-emitting layer. The luminescence may be fluorescence, phosphorescence or both of them, with compounds capable of substantially emitting phosphorescence in the light-emitting layer being preferred.

The organic electroluminescent element of the invention is more preferably an element wherein the light-emitting layer does not contain a fluorescent compound and a phosphorescent compound substantially emits light.

The concentration of the light-emitting material in the light-emitting layer is not particularly limited, but is preferably the same level as, or less than, that of a major component of a host material, more preferably from 0.1% by weight to 50% by weight, still more preferably from 0.2% by weight to 30% by weight, particularly preferably from 0.3% by weight to 20% by weight, most preferably from 0.5% by weight to 10% by weight.

Phosphorescent compounds are not particularly limited, but transition metal complexes are preferred. An iridium complex, a platinum complex, a rhenium complex, a ruthenium complex, a palladium complex, a rhodium complex and a rare earth complex are more preferred, with an iridium complex and a platinum complex being still more preferred. Also, orthometallated iridium complexes having difluorophenylpyridine ligands described in JP-A-2002-235076, JP-A-2002-170684, Japanese Patent Application Nos. 2001-239281 and 2001-248165 are preferred.

Also, phosphorescent compounds described in patent documents such as U.S. Pat. Nos. 6,303,238 and 6,097,147, WO 00/57676, WO 00/70655, WO01/08230, WO01/39234 A2, WO01/41512 A1, WO02/02714 A2, WO02/15645 A1, JP-A-2001-247859, Japanese Patent Application No. 2000-33561, JP-A-2002-117978, Japanese Patent Application No. 2001-248165, JP-A-2002-235076, Japanese Patent Application No. 2001-239281, JP-A-2002-170684, EP 1211257, JP-A-2002-26495, JP-A-2002-234894, JP-A-2001-247859, JP-A-2001-298470, JP-A-2002-173674, JP-A-2002-203678 and JP-A-2002-203679 can preferably be used.

The phosphorescence life (at room temperature) of the phosphorescent compounds to be used in the invention is not particularly limited, but is preferably 1 ms or shorter, more preferably 100 μs or shorter, still more preferably 10 μs or shorter.

$T_1$ level (energy level of the lowest triplet excitation state) of the phosphorescent compound is preferably from 45 kcal/mol (188.3 kJ/mol) to 90 kcal/mol (377.1 kJ/mol), more preferably from 55 kcal/mol (251.0 kJ/mol) to 85 kcal/mol (356.15 kJ/mol), still more preferably from 60 kcal/mol (272.0 kJ/mol) to 85 kcal/mol (355.6 kJ/mol), particularly preferably from 65 kcal/mol (272.35 kJ/mol) to 80 kcal/mol (335.2 kJ/mol).

$T_1$ level (energy level of the lowest triplet excitation state) of a layer adjacent to the light-emitting layer (e.g., a hole transporting layer, an electron transporting layer, a charge blocking layer or an exciton blocking layer) is preferably from 45 kcal/mol (188.3 kJ/mol) to 85 kcal/mol (355.6 kJ/mol), more preferably from 55 kcal/mol (251.0 kJ/mol) to 85 kcal/mol (355.6 kJ/mol), still more preferably from 60 kcal/mol (272.0 kJ/mol) to 85 kcal/mol (355.6 kJ/mol).

The light extraction efficiency of the light-emitting element of the invention can be improved by various known techniques. For example, the light extraction efficiency can be improved by working the substrate surface to form some pattern (for example, to form a fine uneven pattern), controlling the refractive index of the substrate, the ITO layer or the organic layer, thereby the external quantum efficiency being improved.

The light-emitting element of the invention may be of a so-called top-emission system with which luminescence is extracted from the anode side (described in, e.g., JP-A-2003-208109, JP-A-2003-248441, JP-A-2003-257651 and JP-A-2003-282261).

The substrate material to be used in the light-emitting element of the invention is not particularly limited, and may be an inorganic material such as yttria-stabilized zirconia or glass or may be a high-molecular material such as polyester (e.g., polyethylene terephthalate, polybutylene terephthalate or polyethylene naphthalate), polyethylene, polycarbonate, polyether sulfone, polyallylate, allyl diglycol carbonate, polyimide, polycycloolefin, norbornene resin, poly(chlorotrifluoroethylene), polytetrafluoroethylene or polytetrafluoroethylene-polyethylene copolymer.

The organic electroluminescent element of the invention may contain a blue fluorescent compound, or a blue light-emitting element containing the blue fluorescent compound and the light-emitting element of the invention may be used in combination to prepare a multi-color light-emitting device or a full-color light-emitting device.

The light-emitting layer of the organic electroluminescent element of the invention may form a layered structure. The number of layers forming the light-emitting layer is preferably from 2 to 50, more preferably from 4 to 30, still more preferably from 6 to 20.

The thickness of each layer constituting the layered structure is not particularly limited, but is preferably from 0.2 nm to 20 nm, more preferably from 0.4 nm to 15 nm, still more preferably from 0.5 nm to 10 nm, particularly preferably from 1 nm to 5 nm.

The light-emitting layer of the organic electroluminescent element of the invention may have a plurality of domain structures. The light-emitting layer may have other domain structure. For example, the light-emitting layer may be constituted by a region of about 1 $nm^3$ comprising a mixture of a host material A and a light-emitting material B and a region of about 1 $nm^3$ comprising a mixture of a host material C and a light-emitting material D. The size of each domain is preferably from 0.2 nm to 10 nm, more preferably from 0.3 nm to 5 nm, still more preferably from 0.5 nm to 3 nm, particularly preferably from 0.7 nm to 2 nm.

The method for forming the organic layer of the light-emitting layer containing the compound of the invention is not particularly limited, and there may be employed a method of electrical resistance-heated vacuum deposition, an electron beam method, a sputtering method, a molecular lamination method, a coating method (e.g., a spray coating method, a dip coating method, an impregnation method, a roll coating method, a gravure coating method, a reverse coating method, a roll brushing method, an air-knife coating method, a curtain coating method, a spin coating method, a flow coating method, a bar coating method, a micro-gravure coating method, an air doctor coating method, a blade coating method, a squeeze coating method, a transfer roll coating method, a kiss coating method, a cast coating method, an extrusion coating method, a wire-bar coating method or a screen coating method), an inkjet method, a printing method or a transfer method, with an electrical resistance-heated vacuum deposition method, a coating method or a transfer method being preferred in view of characteristic properties and production.

The light-emitting element of the invention is an element wherein a light-emitting layer or a plurality of organic compound films including a light-emitting layer are formed between a pair of electrodes of anode and cathode, and may have a hole injecting layer, a hole transporting layer, an electron injecting layer, an electron transporting layer and a protective layer in addition to the light-emitting layer. Each of these layers may also perform the function of other layer. Various materials may be used for forming individual layers.

The anode supplies holes for a hole injecting layer, a hole transporting layer or a light-emitting layer, and a metal, an alloy, a metal oxide, an electrically conductive compound or a mixture thereof can be used, with materials having a work function of 4 eV or more being preferred. Specific examples thereof include conductive metal oxides such as tin oxide, zinc oxide, indium oxide and indium tin oxide (ITO); metals such as gold, silver, chromium and nickel; mixtures or laminates of the metal and the conductive metal oxide; inorganic conductive substances such as copper iodide and copper sulfide; organic conductive materials such as polyaniline, polythiophene and polypyrrole; and laminates thereof with ITO. Conductive metal oxides are preferred, with ITO being particularly preferred in view of productivity, high conductivity and transparency. The thickness of the anode can properly be selected depending upon materials constituting the anode, but is preferably in the range of from 10 nm to 5 μm, more preferably from 50 nm to 1 μm, still more preferably from 100 nm to 500 nm.

The anode to be used is usually formed as a layer on soda-lime glass, alkali-free glass or a transparent resin substrate. In the case of using glass, alkali-free glass is preferably used in order to reduce the amount of ion to be dissolved out from glass. In the case of using soda-lime glass, it is preferred to form a barrier coat of, for example, silica. The thickness of the substrate is not particularly limited as long as it is enough to provide mechanical strength but, in the case of using glass, the thickness is usually 0.2 mm or more, preferably 0.7 mm or more.

Various methods may be employed for preparing an anode depending upon materials. For example, with ITO, a film is formed by a method of an electron beam method, a sputtering method, an electrical resistance-heated vacuum deposition method, a chemical reaction method (sol-gel method or the like) or a method of coating with an indium tin oxide dispersion.

It is possible to reduce the driving voltage of the element or to enhance light-emitting efficiency by subjecting the anode to a treatment such as washing. For example, with ITO, UV-ozone treatment or plasma treatment is effective.

The cathode supplies electrons for an electron injecting layer, an electron transporting layer or a light-emitting layer, and is selected taking into consideration intimately contacting properties with a layer adjacent to the cathode, such as an electron injecting layer, an electron transporting layer or a light-emitting layer, ionization potential and stability. As a material for the cathode, a metal, an alloy, a metal halide, a metal oxide, an electrically conductive compound or a mixture thereof can be used. Specific examples thereof include alkali metals (e.g., Li, Na and K) and fluorides or oxides thereof, alkaline earth metals (e.g., Mg and Ca) and fluorides or oxides thereof, gold, silver, lead, aluminum, sodium-potassium alloy or a mixture metal thereof, lithium-aluminum alloy or a mixture metal thereof, magnesium-silver alloy or a mixture metal thereof, and rare earth metals such as indium and ytterbium. Those materials which have a work function of 4 eV or less are preferred, and aluminum, lithium-aluminum alloy or a mixture metal thereof, and magnesium-silver alloy or a mixture metal thereof are more preferred. The cathode can have not only a single layer structure of the compound or the mixture described above but a layered structure containing the compound or the mixture described above. For example, a layered structure of aluminum/lithium fluoride or of aluminum/lithium oxide is preferred. The thickness of the cathode can properly be selected depending upon the material, but is preferably in the range of from 10 nm to 5 μm, more preferably from 50 nm to 1 μm, still more preferably from 100 nm to 1 μm.

In preparing the cathode, there may be employed a method of, for example, an electron beam method, a sputtering method, an electrical resistance-heated vacuum deposition method, a coating method or a transfer method. It is possible to vacuum-deposit a metal as a simple substance or to vacuum-deposit two or more components at the same time. It is also possible to form an alloy electrode by simultaneously vacuum-depositing plural kinds of metals. Further, a previously prepared alloy may be vacuum-deposited.

Regarding the sheet resistance of the anode and the cathode, a lower resistance is more preferred, with a resistance of several hundreds Ω/☐ or less being preferred.

Any material may be used for forming the light-emitting layer as long as it can form a layer having the function of injecting holes from the anode, hole injecting layer or hole transporting layer and injecting electrons from the cathode, electron injecting layer or electron transporting layer upon application of voltage, the function of transferring injected charge and the function of providing a site for recombination of hole and electron to generate luminescence. There are illustrated, in addition to the compounds of the invention, benzoxazole, benzimidazole, benzothiazole, styrylbenzene, polyphenyl, diphenylbutadiene, tetraphenylbutadiene, naphthalimide, coumarin, perylene, perinone, oxadiazole, aldazine, pyralidine, cyclopentadiene, bistyrylanthracene, quinacridone, pyrrolopyridine, thiadiazolopyridine, cyclopentadiene, styrylamine, aromatic dimethylidine compounds, various metal complexes represented by 8-quinolinol metal complex or rare earth complex, polymer compounds such as polythiophene, polyphenylene and polyphenylenevinylene, organic silane, iridium-trisphenylpyridine complex, transition metal complexes represented by platinum-porphyrin complex, and derivatives thereof. The thickness of the light-emitting layer is not particularly limited, but is preferably in the range of from 1 nm to 5 µm, more preferably from 5 nm to 1 µm, still more preferably from 10 nm to 500 nm.

The method for forming the light-emitting layer is not particularly limited, and there is employed a method such as an electrical resistance-heated vacuum deposition method, an electron beam method, a sputtering method, a molecular lamination method, a coating method, an inkjet method, a printing method, an LB method or a transfer method, with an electrical resistance-heated vacuum deposition method and a coating method being preferred.

The number of the light-emitting layer may be one or more, and individual layers may emit lights of different colors to generate, for example, white light. It is also possible for a single light-emitting layer to emit white light.

Materials for the hole injecting layer and the hole transporting layer may be those materials which have any of the function of injecting holes from the anode, the function of transporting holes and the function of blocking electrons injected from the cathode. Specific examples thereof include, in addition to the compounds of the invention, carbazole, triazole, oxazole, oxadiazole, imidazole, polyarylalkane, pyrazoline, pyrazolone, phenylenediamine, arylamine, amino-substituted chalcone, styrylanthracene, fluorenone, hydrazone, stilbene, silazane, aromatic tertiary amine compounds, styrylamine compounds, aromatic dimethylidine compounds, porphyrin series compounds, polysilane series compounds, poly(N-vinylcarbazole), aniline series copolymers, thiophene oligomers, electrically conductive high molecular oligomers such as polythiophene, organic silane, carbon film, and derivatives thereof. The thickness of the hole injecting layer and the hole transporting layer is not particularly limited, but is preferably in the range of from 1 nm to 5 µm, more preferably from 5 nm to 1 µm, still more preferably from 10 nm to 500 nm. The hole injecting layer and the hole transporting layer may be of a single layer structure comprising one, two or more kinds of the materials described above, or of a multi-layer structure constituted by a plurality of layers having the same or different formulation.

As a method for forming the hole injecting layer or the hole transporting layer, there is employed a vacuum deposition method, an LB method, a method of coating a solution or dispersion of the hole injecting or transporting material in a solvent, an inkjet method, a printing method or a transfer method. With a coating method, the hole injecting or transporting material can be dissolved or dispersed in a solvent together with a resin component. Examples of the resin component include polyvinyl chloride, polycarbonate, polystyrene, polymethyl methacrylate, polybutyl methacrylate, polyester, polysulfone, polyphenylene oxide, polybutadiene, poly(N-vinylcarbazole), hydrocarbon resin, ketone resin, phenoxy resin, polyamide, ethyl cellulose, vinyl acetate, ABS resin, polyurethane, melamine resin, unsaturated polyester resin, alkyd resin, epoxy resin and silicone resin.

Materials for the electron injecting layer and the electron transporting layer may be those materials which have any of the function of injecting electrons from the cathode, the function of transporting electrons and the function of blocking holes injected from the anode. Specific examples thereof include, in addition to the compounds of the invention, triazole, oxazole, oxadiazole, imidazole, fluorenone, anthraquinodimethane, anthrone, diphenylquinone, thiopyran dioxide, carbodiimide, fluorenylidenemethane, distyrylpyrazine, tetracarboxylic acid anhydrides of aromatic rings such as naphthalene and perylene, phthalocyanine, various metal complexes represented by metal complexes of 8-quinolinol, metal phthalocyanines and metal complexes having benzoxazole or benzothiazole as a ligand, organic silanes and derivatives thereof. The thickness of the electron injecting layer and the electron transporting layer is not particularly limited, but is preferably in the range of from 1 nm to 5 µm, more preferably from 5 nm to 1 µm, still more preferably from 10 nm to 500 nm. The electron injecting layer and the electron transporting layer may be of a single layer structure comprising one, two or more kinds of the materials described above, or of a multi-layer structure constituted by a plurality of layers having the same or different formulation.

As a method for forming the electron injecting layer or the electron transporting layer, there is employed a vacuum deposition method, an LB method, a method of coating a solution or dispersion of the electron injecting or transporting material in a solvent, an inkjet method, a printing method or a transfer method. With a coating method, the electron injecting or transporting material can be dissolved or dispersed in a solvent together with a resin component. As the resin component, those which have been illustrated with respect to the hole injecting or transporting layer can be employed.

As materials for the protective layer, those materials may be employed which prevent substances accelerating deterioration of the element, such as water or oxygen, from entering into the element. Specific examples thereof include metals such as In, Sn, Pb, Au, Cu, Ag, Al and Ni; metal oxides such as MgO, SiO, $SiO_2$, $Al_2O_3$, GeO, NiO, CaO, BaO, $Fe_2O_3$, $Y_2O_3$ and $TiO_2$; metal fluorides such as $MgF_2$, LiF, $AlF_3$ and $CaF_2$; nitrides such as $SiN_x$ and $SiO_xN_y$; polyethylene; polypropylene; polymethyl methacrylate; polyimide; polyurea; polytetrafluoroethylene; polychlorotrifluoroethylene; polydichlorodifluoroethylene; chlorotrifluoroethylene/dichlorodifluoroethylene copolymer; copolymers obtained by copolymerizing a monomer mixture containing tetrafluoroethylene and at least one comonomer; fluorine-containing copolymers having a cyclic structure in the copolymer main chain; water-absorbing substances of 1% or more in water absorption; and moisture-proof substances of 0.1% or less in water absorption.

The method for forming the protective layer is not particularly limited, either, and there may be employed a method such as a vacuum deposition method, a sputtering method, a reactive sputtering method, an MBE (molecular beam epitaxy) method, a cluster ion beam method, an ion plating method, a plasma polymerization method (high frequency excitation ion plating method), a plasma CVD method, a laser CVD method, a thermal CVD method, a gas source CVD method, a coating method, a printing method or a transfer method.

Use of the light-emitting element of the invention is not particularly limited, and can preferably be used in the field of display element, display, backlight, electrophotography, light source for illumination, light source for recording, light source for exposure, light source for reading, signs, signboards, interior, optical communication or the like.

Specific examples of the invention will be described below. However, embodiments of the invention are not limited only to them.

Example 1

Element 1 of Invention

A washed ITO substrate was placed in a vacuum deposition apparatus, and α-NPD was vacuum deposited thereon in a thickness of 40 nm. FIrpic (phosphorescent compound), compound (3) and mCP were vacuum deposited thereon in a thickness of 30 nm with a ratio (by weight) of 6:20:74, Balq was vacuum deposited thereon in a thickness of 6 nm, and Alq was vacuum deposited thereon in a thickness of 20 nm. Magnesium and silver were vacuum co-deposited in a thickness of 100 nm with a ratio (molar ratio) of 10:1 to prepare an EL element. Additionally, the lowest triplet energy of the compound (3) in a film state is 71.5 kcal/mol.

When a direct current constant voltage was applied to the EL element by using a source measure unit manufactured by TOYO Corporation to emit light, a light having a maximum light-emitting wavelength at around 485 nm was emitted.

As to driving durability of the element 1 of the invention, the luminance half-life period of the element measured with an initial luminance of 300 cd/m² was found to be about ten times as long as that of the element of Comparative Example 1.

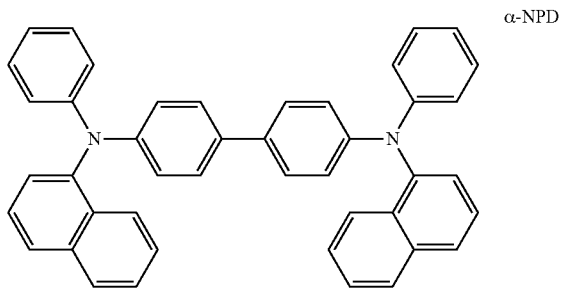

α-NPD

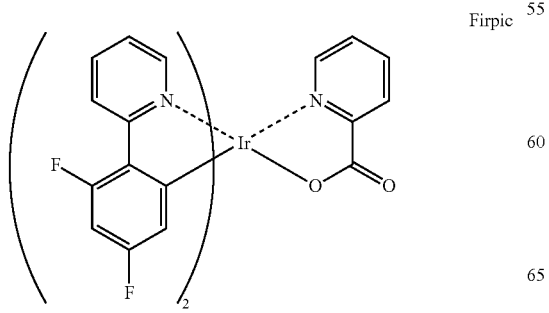

FIrpic

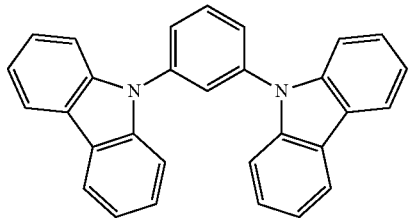

mCP

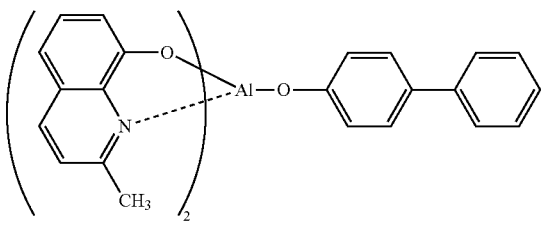

Balq

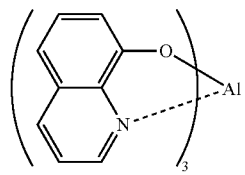

Alq

Example 2

Element 2 of Invention

A light-emitting element was prepared in the same manner as in Example 1 except for using compound (4) in place of compound (3) in preparation of the light-emitting element in Example 1. When the resulting element was allowed to emit light in the same manner as in Example 1, a light having a maximum light-emitting wavelength at around 485 nm was emitted. Additionally, the lowest triplet energy of the compound (4) in a film state is 71 kcal/mol.

As to driving durability of the element 2 of the invention, the luminance half-life period of the element measured with an initial luminance of 300 cd/m² was found to be about ten times as long as that of the element of Example 4 (Comparative Example 1).

Example 3

Element 3 of the Invention

A light-emitting element was prepared in the same manner as in Example 1 except for using BAlq:compound (3)=80:20 (by weight) in place of BAlq in preparation of the light-emitting element in Example 1. When the resulting element was allowed to emit light in the same manner as in Example 1, a light having a maximum light-emitting wavelength at around 485 nm was emitted. The external quantum efficiency of the element was found to be about 1.5 times as much as that of the element of Example 1.

Example 4

Comparative Element 1

A light-emitting element was prepared in the same manner as in Example 1 except for using compound A in place of compound (3) in preparation of the light-emitting element in Example 1. When the resulting element was allowed to emit light in the same manner as in Example 1, a light having a maximum light-emitting wavelength at around 485 nm was emitted.

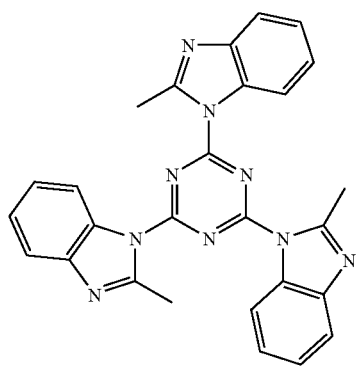

Compound A

Example 5

Preparation of Comparative Element B-1

A glass substrate (manufactured by Geomatec Co., Ltd.; surface resistance: 10 Ω/sq) which includes an ITO film having 0.5 mm thickness and 2.5 cm square was placed in a washing vessel, and subjected to an ultrasonic cleaning in 2-propanol and an UV-ozone treatment for 30 minutes. The following organic compound layers were deposited in the order on the transparent anode (ITO film) by means of a vacuum deposition method.

(First layer): film thickness of 120 nm

HIL-A (Second layer): film thickness of 10 nm

α-NPD (Third layer): film thickness of 30 nm

CBP=90 mass %

Firpic=10 mass %

(Fourth layer): film thickness of 40 nm

BAlq

Finally, 0.5 nm of lithium fluoride and 100 nm of metallic aluminum were deposited in the said order to form a cathode.

The resultant was placed into a glove box substituted by an argon gas without bringing into contact with air, and sealed with a stainless steel sealing canister and a UV-curable adhesive (XNR5516HV, produced by Nagase Chiba Co., Ltd) to obtain a comparative element B-1.

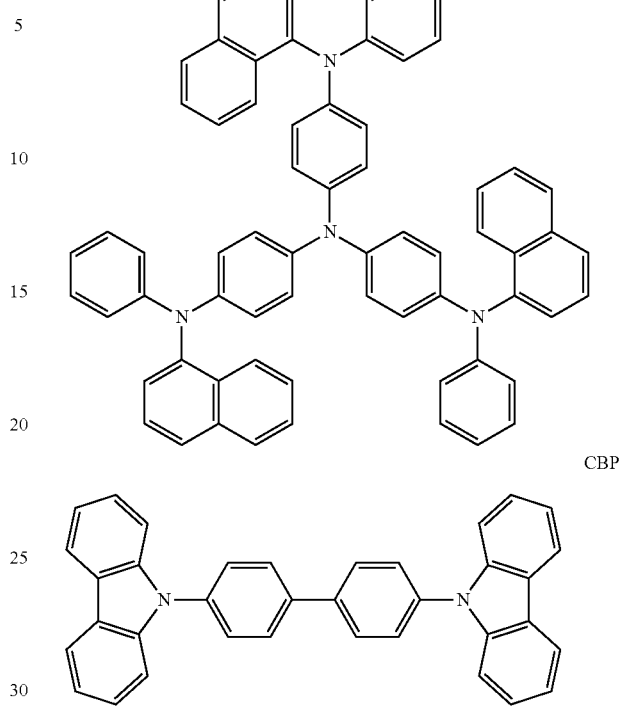

Examples 6 and 7

Preparation of Comparative Elements J-1 and J-2 of Present Invention

Organic electroluminescent elements J-1 and J-2 of the invention were prepared in the same manner as the comparative element B-1, except that the CBP was changed to the illustrative compound (3) and the illustrative compound (31), respectively.

[Evaluation of Organic Electroluminescent Elements J-1 and J-2]

When a constant voltage was applied at 1V interval from 1V to 20V to the comparative element B-1, and the elements J-1 and J-2 of the invention, an emission of light derived from Firpic was observed in any of those elements. The maximum values of the external quantum efficiency were 3.2%, 7.4%, and 8.0%, respectively, and the elements J-1 and J-2 of the invention had 2 times or more greater value than that of the comparative element B-1. Additionally, the lowest triplet energy of the compound (31) in a film state is 69 kcal/mol.

Example 8

Preparation of Comparative Element B-2

A glass substrate (manufactured by Geomatec Co., Ltd.; surface resistance: 10 Ω/sq) which includes an ITO film having 0.5 mm thickness and 2.5 cm square was placed in a washing vessel, and subjected to an ultrasonic cleaning in 2-propanol and an UV-ozone treatment for 30 minutes. The following organic compound layers were deposited in the order on the transparent anode (ITO film) by means of a vacuum deposition method.

(First layer): film thickness of 120 nm
HIL-A
(Second layer): film thickness of 10 nm
NPD
(Third layer): film thickness of 30 nm
mCP=90 mass %
EML-A=10 mass %
(Fourth layer): film thickness of 10 nm
BAlq
(Fifth layer): film thickness of 30 nm
Alq Finally, 0.5 nm of lithium fluoride and 100 nm of metallic aluminum were deposited in the said order to form a cathode.

The resultant was placed into a glove box substituted by an argon gas without bringing into contact with air, and sealed with a stainless steel sealing canister and a UV-curable adhesive (XNR5516HV, produced by Nagase Chiba Co., Ltd) to obtain a comparative element B-2.

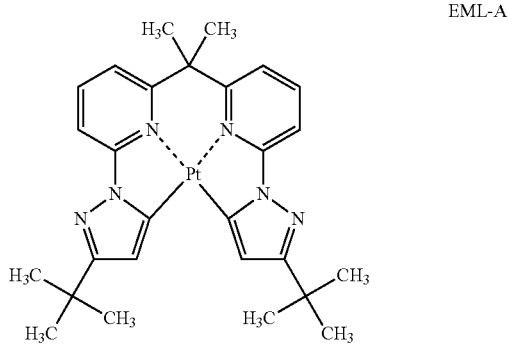

EML-A

Example 9

Preparation of Comparative Element J-3 of the Present Invention

The organic electroluminescent element J-3 of the invention was prepared in the same manner as the comparative element B-2, except that the BAlq was changed to the illustrative compound (31).

[Evaluation of Organic Electroluminescent Element J-3]

When a constant voltage was applied at 1V interval from 1V to 20V to the comparative element B-2 and the element J-3 of the invention, an emission of light derived from EML-A was observed in any of those elements. The maximum values of the external quantum efficiency were 4.4% and 11.5%, respectively, and the element J-3 of the invention had 2.5 times or more greater value than that of the comparative element B-2.

The invention can provide a light-emitting element which can emit light with high efficiency and high durability.

The entire disclosure of each and every foreign patent application from which the benefit of foreign priority has been claimed in the present application is incorporated herein by reference, as if fully set forth.

What is claimed:

1. An organic electroluminescent element comprising:
a pair of electrodes; and
one or more organic compound layers at least one of which is a light-emitting layer, the one or more organic compound layers being provided between the pair of electrodes,
wherein at least one of the one or more organic compound layers comprises a compound represented by general formula (Z):

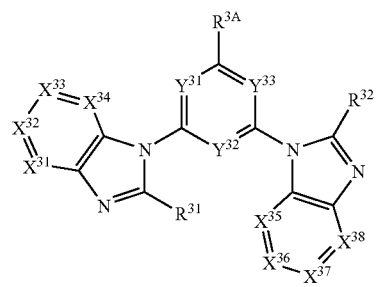

general formula (Z)

wherein $R^{31}$ and $R^{32}$ each represents an alkyl group, a perfluoroalkyl group, an aryl group, a hetero ring group, an alkenyl group, an alkoxy group, an aryloxy group, an alkylamino group, an arylamino group, a hetero ring amino group, a silicon-containing hetero ring group, a silyl group, a hydroxyl group, a mercapto group, or a halogen atom, $R^{3A}$ represents a substituent other than an aromatic hetero ring connected through a nitrogen atom, or a hydrogen atom, $X^{31}$ to $X^{38}$ each represents a substituted or unsubstituted carbon atom or a nitrogen atom, and $Y^{31}$ to $Y^{33}$ each represents a nitrogen atom or C—$R^{3B}$, wherein $R^{3B}$ represents a substituent other than an aromatic hetero ring connected through a nitrogen atom, or a hydrogen atom.

2. The organic electroluminescent element as described in claim 1,
wherein the compound represented by the general formula (Z) is a compound represented by the following general formula (Z-2):

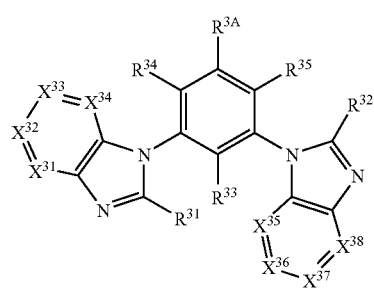

general formula (Z-2)

wherein $R^{31}$ and $R^{32}$ each represents an alkyl group, a perfluoroalkyl group, an aryl group, a hetero ring group, an alkenyl group, an alkoxy group, an aryloxy group, an alkylamino group, an arylamino group, a hetero ring amino group, a silicon-containing hetero ring group, a silyl group, a hydroxyl group, a mercapto group, or a halogen atom, $R^{33}$ to $R^{35}$ and $R^{3A}$ each represents a substituent other than an aromatic hetero ring connected through a nitrogen atom, or a hydrogen atom, and $X^{31}$ to $X^{38}$ each represents a substituted or unsubstituted carbon atom or a nitrogen atom.

3. The organic electroluminescent element as described in claim 2,
wherein the compound represented by the general formula (Z-2) is a compound represented by the following general formula (Z-3):

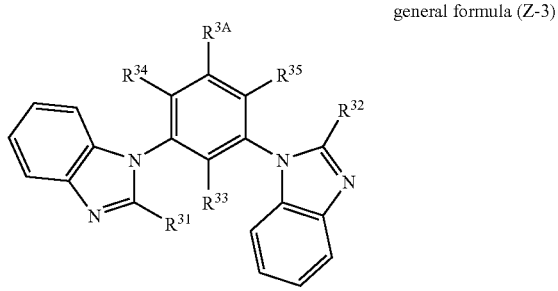

general formula (Z-3)

wherein $R^{31}$ and $R^{32}$ each represents an alkyl group, a perfluoroalkyl group, an aryl group, a hetero ring group, an alkenyl group, an alkoxy group, an aryloxy group, an alkylamino group, an arylamino group, a hetero ring amino group, a silicon-containing hetero ring group, a silyl group, a hydroxyl group, a mercapto group, or a halogen atom, and $R^{33}$ to $R^{35}$ and $R^{3A}$ each represents a substituent other than an aromatic hetero ring connected through a nitrogen atom, or a hydrogen atom.

4. The organic electroluminescent element as described in claim 1,
wherein the light-emitting layer comprises a compound capable of generating luminescence by a transition from a triplet excitation state thereof.

5. The organic electroluminescent element as described in claim 1, wherein the compound represented by the general formula (Z) is contained in the light-emitting layer.

6. The organic electroluminescent element as described in claim 1,
wherein the compound represented by the general formula (Z) is contained in one of the organic compound layers which is adjacent to the light-emitting layer.

7. The organic electroluminescent element as described in claim 1, wherein the lowest triplet energy level of the compound represented by the general formula (Z) is 65 kcal/mol or more.

8. The organic electroluminescent element as described in claim 1, wherein $R^{31}$ and $R^{32}$ each represents an alkyl group or an aryl group.

9. A compound represented by the general formula (Z):

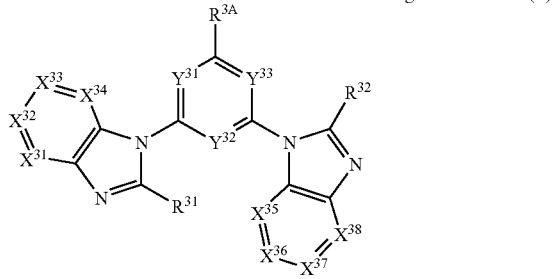

general formula (Z)

wherein $R^{31}$ and $R^{32}$ each represents an alkyl group or an aryl group, $R^{3A}$ represents a substituent other than an aromatic hetero ring connected through a nitrogen atom, or a hydrogen atom, $X^{31}$ to $X^{38}$ each represents a substituted or unsubstituted carbon atom or a nitrogen atom, and $Y^{31}$ to $Y^{33}$ each represents a nitrogen atom or C—$R^{3B}$, wherein $R^{3B}$ represents a substituent other than an aromatic hetero ring connected through a nitrogen atom, or a hydrogen atom.

10. A compound represented by the following general formula (Z-2):

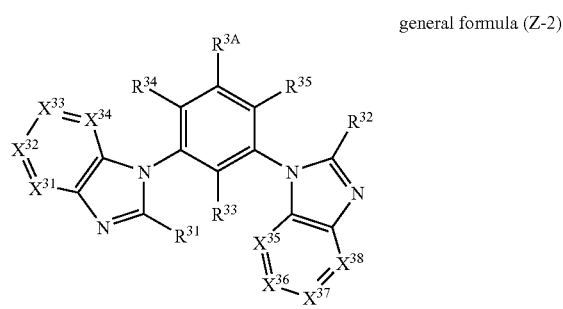

general formula (Z-2)

wherein $R^{31}$ and $R^{32}$ each represents an alkyl group or an aryl group, $R^{33}$ to $R^{35}$ and $R^{3A}$ each represents a substituent other than an aromatic hetero ring connected through a nitrogen atom, or a hydrogen atom, and $X^{31}$ to $X^{38}$ each represents a substituted or unsubstituted carbon atom or a nitrogen atom.

11. A compound represented by the following general formula (Z-3):

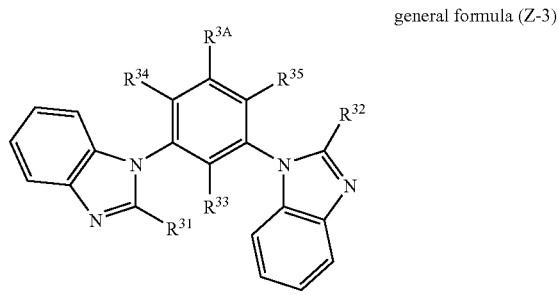

general formula (Z-3)

wherein $R^{31}$ and $R^{32}$ each represents an alkyl group or an aryl group, and $R^{33}$ to $R^{35}$ and $R^{3A}$ each represents a substituent other than an aromatic hetero ring connected through a nitrogen atom, or a hydrogen atom.

* * * * *